US006254468B1

(12) United States Patent
Gozzi et al.

(10) Patent No.: US 6,254,468 B1
(45) Date of Patent: Jul. 3, 2001

(54) METHOD FOR THE MANUFACTURE OF DENTAL TOOLS FOR THE TREATMENT OF SURFACES

(75) Inventors: Guido Gozzi, Dietlikon; Heinrich Rupf, Buchs; Beat A. Von Weissenfluh, Gentilino, all of (CH)

(73) Assignee: Identoflex AG, Hünenberg (CH)

( * ) Notice: Subject to any disclaimer, the term of this patent is extended or adjusted under 35 U.S.C. 154(b) by 0 days.

(21) Appl. No.: 09/352,843

(22) Filed: Jul. 13, 1999

(30) Foreign Application Priority Data

Jul. 13, 1998 (CH) .................................................. 1497/98

(51) Int. Cl.[7] ............................ B24D 11/00; B24D 15/00; A61C 3/02
(52) U.S. Cl. .......................... 451/526; 451/533; 451/539; 451/541; 451/544; 451/548; 433/134; 433/165; 433/166; 51/299
(58) Field of Search .................................. 451/526, 533, 451/539, 541, 544, 548; 433/134, 166, 165; 51/299, 295

(56) References Cited

U.S. PATENT DOCUMENTS

| 22,606 | * | 1/1859 | Mayall | 433/165 |
|---|---|---|---|---|
| 95,823 | * | 10/1869 | Merrick | 451/548 |
| 133,617 | * | 12/1872 | Arthur | 451/548 |
| 170,178 | * | 11/1875 | Locke | 433/165 |
| 190,115 | * | 5/1877 | Babcock et al. | 451/548 |
| 205,462 | * | 7/1878 | Arthur | 451/548 |
| 207,079 | * | 8/1878 | Starr | 451/548 |
| 261,198 | * | 7/1882 | Barton | 451/548 |
| 302,952 | * | 8/1884 | Smith | 451/548 |
| 382,609 | * | 5/1888 | Holbrook | 451/548 |
| 391,302 | * | 10/1888 | Deane | 451/548 |
| 440,682 | * | 11/1890 | Wood | 451/548 |
| 534,540 | * | 2/1895 | Wooster | 451/548 |
| 583,735 | * | 6/1897 | Dodge | 451/548 |
| 662,538 | * | 11/1900 | Le Cron | 451/548 |
| 706,013 | * | 8/1902 | Boyce | 433/165 |
| 783,959 | * | 2/1905 | Hull | 451/548 |
| 1,644,465 | * | 10/1927 | Chott | 433/165 |
| 1,707,162 | * | 3/1929 | Hudspith | 451/548 |
| 1,809,907 | * | 6/1931 | Newcomb | 433/165 |
| 2,015,727 | * | 10/1935 | Prey | 451/548 |
| 2,181,474 | * | 11/1939 | Berger | 451/548 |
| 2,324,377 | * | 7/1943 | Fischer | 451/548 |
| 2,366,767 | * | 1/1945 | Brooks | 451/548 |
| 2,393,751 | * | 1/1946 | Chott | 433/165 |
| 2,431,369 | * | 11/1947 | Chiles | 451/548 |

(List continued on next page.)

FOREIGN PATENT DOCUMENTS 295 08 070 U   9/1995 (DE) .
198143         5/1923 (GB) .

Primary Examiner—M. Rachuba
(74) Attorney, Agent, or Firm—Young & Thompson

(57) ABSTRACT

In the method for the manufacture of dental tools for the treatment of surfaces, a rubber core serving as a carrier layer is first applied by injection molding onto the spindle of the tool, and the abrasive layer comprising the abrasive grains is subsequently applied to the carrier layer. In another method for the manufacture of dental tools for different treatments of surfaces, more particularly for coarse grinding, finishing, and polishing, rubber-elastic masses of different degrees of hardness are used for the abrasive parts of the tools according to the intended treatment, and abrasive grains of the same size are embedded in the rubber-elastic mass of these parts. In a preferred method, the two mentioned methods are combined to create dental tools which either comprise a combination of a carrier layer and of a plurality of overlying abrasive parts having different degrees of hardness and the same grain size, or which consist of a set of tools comprising respective tools composed of a carrier layer and an abrasive layer having different degrees of hardness of the embedding mass but the same grain size of the abrasive grains.

15 Claims, 1 Drawing Sheet

U.S. PATENT DOCUMENTS

| | | | |
|---|---|---|---|
| 2,552,485 | * | 5/1951 | Howard et al. .......................... 451/548 |
| 2,842,844 | * | 7/1958 | Seal ........................................ 433/166 |
| 2,906,612 | * | 9/1959 | Anthony et al. ....................... 451/548 |
| 3,142,138 | * | 7/1964 | Kean et al. ............................. 451/548 |
| 3,243,925 | * | 4/1966 | Buzzell ................................... 433/166 |
| 3,461,563 | * | 8/1969 | Nelson .................................... 451/548 |
| 3,775,848 | * | 12/1973 | Barnett .................................... 433/165 |
| 3,858,368 | * | 1/1975 | Cocherell et al. ...................... 433/165 |
| 3,894,339 | * | 7/1975 | Manzi ..................................... 433/165 |
| 3,924,362 | * | 12/1975 | McAleer .................................. 51/296 |
| 4,055,897 | * | 11/1977 | Brix ........................................ 451/533 |
| 4,447,208 | * | 5/1984 | Kawai ..................................... 433/166 |
| 4,539,017 | * | 9/1985 | Augustin .................................. 51/293 |
| 4,830,615 | * | 5/1989 | Feinman et al. ....................... 433/166 |
| 4,988,294 | * | 1/1991 | Dube et al. ............................ 433/134 |
| 5,273,559 | * | 12/1993 | Hammar et al. ......................... 51/298 |
| 5,369,916 | * | 12/1994 | Jefferies et al. ....................... 451/526 |
| 5,882,201 | * | 3/1999 | Salem ..................................... 433/166 |

* cited by examiner

METHOD FOR THE MANUFACTURE OF DENTAL TOOLS FOR THE TREATMENT OF SURFACES

FIELD OF THE INVENTION

The present invention refers to a method for the manufacture of dental tools for the treatment of surfaces, more particularly comprising a rubber-elastic mass in which the abrasive grains are enclosed.

The present inventions refers also to a method for the manufacture of dental tools for different treatments of surfaces, more particularly for coarse grinding, finishing, and polishing, comprising at least one abrasive portion in which the abrasive grains are enclosed, as well as to tools manufactured according to the method.

The present invention particularly refers to dental tools for finishing and polishing ceramic or composite surfaces of tooth fillings.

BACKGROUND OF THE INVENTION

Generally, for the coarse treatment and for finishing or polishing the surfaces of ceramic or composite fillings, dental tools, hereinafter called rubber polishers or polishers for the sake of simplicity, are used which comprise a rubber-elastic mass in which abrasive grains are embedded. According to the fineness of the grain, these tools are used for the coarse treatment or for finishing or polishing operations. The size of grain ranges from approx. 320 $\mu$ down to 5 $\mu$.

Usually, the application of rubber polishers is recommended between the coarse treatment and the final high polishing. In the case of metal, high gloss may even be obtained with rubber polishers alone. The rubber polishers have different typical shapes which are determined by the anatomic structure and the specific morphology of the polished teeth and replacements such as fillings. These typical shapes in turn are subject to wear according to typical abrasion patterns. If the abrasion exceeds a certain degree, the polisher becomes useless and has to be replaced by a new one. Depending on the typical shape, the worn portions represent a greater or smaller part of the entire polisher.

The abrasive properties of the polishers are achieved by embedding abrasive grains in the rubber-elastic mass. In all tools of the prior art, the entire polishing mass is filled with abrasive grains regardless of the portions of the polisher which are typically used or not. Particularly if diamond grains are used, this leads to relatively expensive tools.

SUMMARY OF THE INVENTION

On the background of this prior art, it is a first object of the invention to provide a method for the manufacture of dental tools, and dental tools manufactured according to the method which offer a substantial economy as compared to known methods and tools. This object is attained by a method wherein a carrier layer is first applied to the spindle of the tool, and the abrasive layer comprising abrasive grains is subsequently applied to the carrier layer.

Rubber polishers have various typical shapes which are determined by the anatomical structures and the specific morphology of the polished teeth and replacements. According to the prior art, the varying abrasive properties of rubber polishers for dentistry and dental technique are determined by abrasive grains of varying size. However, this principle only works if the rubber matrix of the polishers has a certain hardness. Therefore, rubber polishers of the prior art always have a minimal hardness, which is disadvantageous especially for clinical dental applications. The friction of the dental tool on the tooth and thus its heating are inconveniently high, its adjustment to the surface is insufficient, and the abrasion of the polishers is increased.

On the background of this prior art, it is another object of the invention to simplify the method for the manufacture of dental tools and to avoid the described drawbacks. This object is attained by a method wherein rubber-elastic masses of different degrees of hardness are used for the abrasive parts of the tools according to the intended treatment, and abrasive grains of the same size are embedded in the rubber-elastic masses of said parts. The solution according to this method is based upon the discovery that the abrasive properties of abrasive grains are not so much a function of the grain size but rather of the support, i.e. of the rubber-elastic mass in which the grains are embedded.

BRIEF DESCRIPTION OF THE DRAWINGS

The invention is explained in more detail hereinafter with reference to a drawing of two exemplary embodiments.

DETAILED DESCRIPTION OF THE INVENTION

Figure 1:
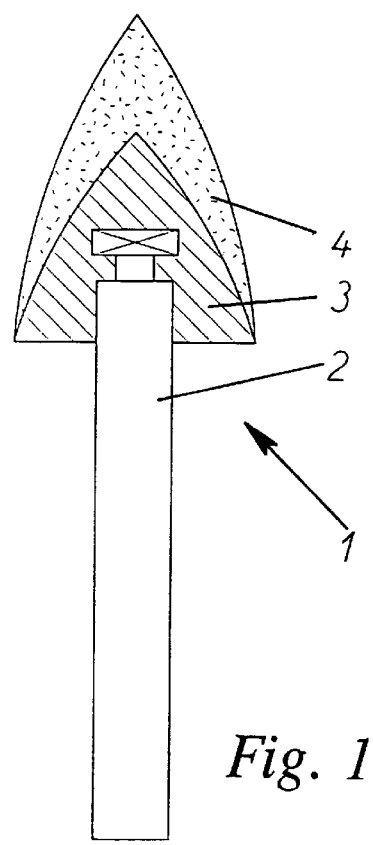
FIG. 1 shows the structure of a dental tool manufactured according to one embodiment of the invention; in a schematic cross-sectional view.

FIG. 1 illustrates a dental tool 1 having a known spindle 2 allowing its connection to the handpiece of a dental apparatus. In contrast to the tools of the prior art, spindle 2 is provided with a carrier layer 3 on which the proper abrasive layer 4 is applied. It is apparent that only abrasive layer 4 of this dental tool is used for abrasive purposes while the carrier layer 3 is not. A considerable reduction of the amount of diamond grains or other abrasive grains is therefore possible due to the fact that only a relatively thin layer, namely the abrasive layer, is provided with such grains.

It is advantageous, but not compulsory, that the carrier layer consists of the same rubber-elastic material as the abrasive layer since the bond between the layers is free of problems in this case. As to the rubber-elastic material, all elastomeric plastic materials known for this application are possible and will be called rubber hereinafter for the sake of simplicity. Therefore, the carrier layer is in fact a rubber core.

The manufacture is effected as described above, i.e. carrier layer 3, an unfilled rubber core, is first applied by injection molding onto the spindle, and in a second step, the thinner abrasive layer 4 is applied, e.g. by means of a molding press. This is also possible with the disk-shaped tool 5 according to FIG. 3 where abrasive layer 6 is a relatively thin ring which is also applied to carrier layer 7, i.e. the rubber core, by a molding press, for example, whereas the rubber core is applied by injection molding onto spindle 2.

Figure 3:
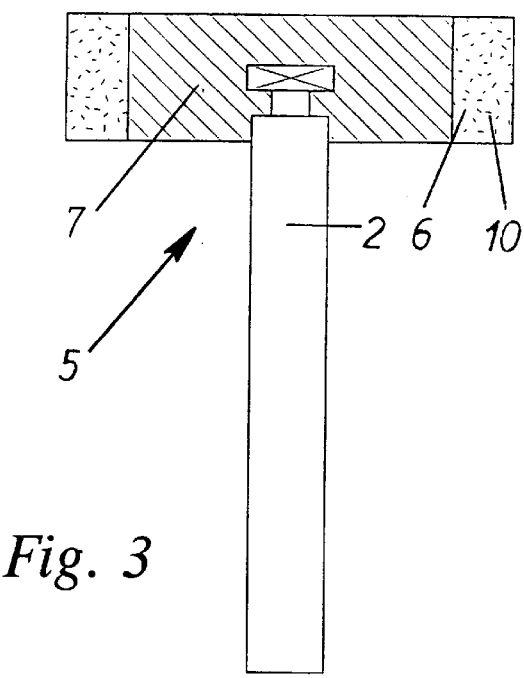
FIG. 3 shows an alternative embodiment of FIG. 2.

It is obvious that the tool shapes and types are not limited to those of FIG. 1 or 3 and that the manufacturing method includes dental tools of all forms.

In the manufacture of tools having heterogeneous abrasive properties, it has been found that the principle of minimal hardness mentioned in the introduction is overruled by another principle when the elasticity of the rubber exceeds a certain threshold. At that point, the size of grains becomes irrelevant since the grains may evade the polishing action on account of the softness of the rubber mass. The abrasive effect is decreasing and becomes a polishing effect which is not a function of the size of the abrasive grains but of the elasticity of the rubber-elastic material carrying the grains.

It follows that the polishing degree can be varied with one and the same grain and that different abrasive properties can be incorporated in the same polisher by using parts of different elasticity while maintaining the grain size. Also, separate polishers may be designed, i.e. graded according to this principle.

Figure 2:
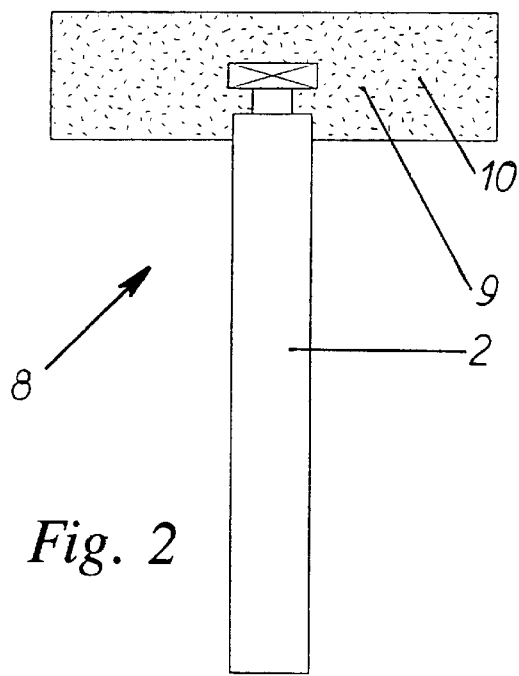
FIG. 2 shows a schematic cross-sectional view of another dental tool manufactured according to another embodiment of the invention.

This is schematically and symbolically indicated in FIG. 2 by dental tool 8 which comprises an abrasive layer in the form of embedding mass 9 in which abrasive grains of the same size, e.g. diamond grains 10, are embedded.

However, the tool may also be designed as shown in FIG. 3, i.e. abrasive layer 6 comprises the same abrasive grains 10 as in FIG. 2, but it is applied by injection molding onto a carrier layer 7, i.e. the rubber core.

The different tools according to FIG. 2 or 3 may include the same grains 10 throughout, however in different embedding masses 11,12 which determine the polishing degree, or they may correspond to the tool of FIG. 1 and comprise an abrasive layer 4 including grains of the same size but different embedding masses of different degrees of hardness.

As follows from the above description, on one hand, the dental tools may be manufactured according to a method which allows a reduced amount of abrasive grains, i.e. they are composed of a carrier layer and an abrasive layer; in the first case, depending on the application, the abrasive layer includes grains of different size but an embedding mass of a uniform minimal hardness. On the other hand, the tools may be so designed that they comprise only an abrasive layer which is applied to the spindle, the respective abrasive layer including grains of the same size but embedding masses of different degrees of hardness; these may be distinct tools or tools having different layers comprising embedding masses of different degrees of hardness.

However, the described methods also allow to combine the two advantages, as illustrated by the tool according to FIG. 3 which comprises a carrier layer 7 free of abrasive grains and one or several overlying abrasive layers 6 including grains of the same size but embedding masses of different degrees of hardness in region 11 and 12. As previously mentioned, the dental tools according to FIG. 3 or according to FIG. 1 may have any other desired shape.

In the manufacture, it is possible to use different colorations both for the carrier layer and for the different degrees of hardness of the embedding mass.

What is claimed is:

1. A method for the manufacture of dental tools for the treatment of surfaces, comprising the steps of:
  applying a carrier layer of a rubber-elastic mass to a spindle of a tool; and
  subsequently applying an abrasive layer comprising abrasive grains embedded in a rubber-elastic mass to the carrier layer.

2. A method for the manufacture of dental tools for the treatment of surfaces, comprising the steps of:
  applying an abrasive layer comprising abrasive grains embedded in a rubber-elastic mass to a spindle of a plurality of tools
  wherein rubber-elastic masses of different degrees of hardness are used for each tool, and abrasive grains of the same size are used for each tool.

3. The method of claim 2, wherein at least one of the tools is made with plural abrasive portions comprising rubber-elastic masses of different degrees of hardness and abrasive grains of the same kind.

4. A method for the manufacture of dental tools for the treatment of surfaces, comprising applying a carrier layer of a rubber-elastic mass to a spindle of a plurality of tools and applying an abrasive layer comprising abrasive grains embedded in a rubber-elastic mass to the carrier layer of each tool and wherein rubber-elastic masses of different degrees of hardness are used for the abrasive layers of the tools, and abrasive grains of the same size are embedded in the rubber-elastic masses of the tools.

5. The method of claim 4, wherein at least one of the tools is made with plural abrasive portions comprising rubber-elastic masses of different degrees of hardness.

6. A dental tool manufactured according to the method of claim 1, comprising a carrier layer applied to a spindle, and an abrasive layer applied to the carrier layer.

7. A dental tool manufactured according to the method of claim 3, comprising a plurality of abrasive portions, wherein the abrasive portions comprise masses of different degrees of hardness and abrasive grains of the same kind.

8. A set of dental tools of different abrasive properties manufactured according to the method of claim 3, wherein each abrasive portion of the dental tools of a set comprises a mass of a different hardness degree and abrasive grains of the same kind.

9. A dental tool manufactured according to the method of claim 1, comprising a carrier layer applied to a spindle, an abrasive layer applied to the carrier layer, wherein the abrasive layer comprises a plurality of portions having rubber-elastic masses of different degrees of hardness and abrasive grains of the same kind.

10. A set of dental tools manufactured according to the method of claim 1, comprising a carrier layer applied to a spindle, an abrasive layer applied to the carrier layer, and wherein each abrasive portion of the dental tools of a set comprises a mass of a different hardness degree and abrasive grains of the same kind.

11. A set of dental tools manufactured according to the method of claim 3, comprising a carrier layer applied to a spindle, an abrasive layer applied to the carrier layer, and wherein each abrasive portion of the dental tools of a set comprises a mass of a different hardness degree and abrasive grains of the same kind.

12. The method of claim 1, wherein the abrasive grains are distributed throughout the rubber-elastic mass of the abrasive layer.

13. The method of claim 1, wherein the carrier layer is applied to the spindle by injection molding.

14. The method of claim 13, wherein the abrasive layer is applied to the carrier layer by press molding.

15. The method of claim 13, wherein the abrasive layer is applied to the carrier layer by injection molding.

* * * * *